(12) United States Patent
Sheskey et al.

(10) Patent No.: US 8,778,399 B2
(45) Date of Patent: Jul. 15, 2014

(54) IN SITU, LIQUID-ACTIVATED FILM COATED TABLETS AND A PROCESS FOR MAKING THE SAME

(75) Inventors: Paul J. Sheskey, Midland, MI (US); Colin M. Keary, Greenville, SC (US)

(73) Assignee: Dow Global Technologies LLC, Midland, MI (US)

( * ) Notice: Subject to any disclaimer, the term of this patent is extended or adjusted under 35 U.S.C. 154(b) by 502 days.

(21) Appl. No.: 12/665,499

(22) PCT Filed: Jun. 2, 2008

(86) PCT No.: PCT/US2008/065478
§ 371 (c)(1),
(2), (4) Date: May 5, 2010

(87) PCT Pub. No.: WO2009/005923
PCT Pub. Date: Jan. 8, 2009

(65) Prior Publication Data
US 2010/0215812 A1  Aug. 26, 2010

Related U.S. Application Data

(60) Provisional application No. 60/948,110, filed on Jul. 5, 2007.

(51) Int. Cl.
*A61K 9/14* (2006.01)

(52) U.S. Cl.
USPC .......................................................... 424/488

(58) Field of Classification Search
USPC .......................................................... 424/488
See application file for complete search history.

(56) References Cited

U.S. PATENT DOCUMENTS

| | | | |
|---|---|---|---|
| 3,653,914 A | 4/1972 | Schmitt | |
| 3,981,984 A | 9/1976 | Signorinio | |
| 4,060,645 A | 11/1977 | Risler et al. | |
| 4,226,849 A * | 10/1980 | Schor | 424/469 |
| 4,540,566 A * | 9/1985 | Davis et al. | 424/480 |
| 4,645,812 A | 2/1987 | Maier | |
| 4,704,295 A | 11/1987 | Porter et al. | |
| 4,828,841 A | 5/1989 | Porter et al. | |
| 5,011,694 A | 4/1991 | Nuernberg et al. | |
| 5,077,053 A | 12/1991 | Kuncewitch et al. | |
| 5,432,215 A | 7/1995 | Girg et al. | |
| 6,264,989 B1 | 7/2001 | Kato et al. | |
| 6,482,433 B1 | 11/2002 | DeRoos et al. | |
| 2004/0121154 A1 | 6/2004 | Bretschneider et al. | |
| 2004/0247679 A1 | 12/2004 | Lin et al. | |
| 2006/0078663 A1 | 4/2006 | Propst et al. | |

FOREIGN PATENT DOCUMENTS

| | | |
|---|---|---|
| GB | 937564 | 9/1961 |
| JP | 8-291051 A | 11/1996 |
| JP | 9-48726 A | 2/1997 |
| JP | 10-57449 A | 3/1998 |
| WO | 99/47126 A1 | 9/1999 |

OTHER PUBLICATIONS

Ekube et al. (International Journal of Pharmaceutics 156 (1997) 49-57).*

* cited by examiner

*Primary Examiner* — David J Blanchard
*Assistant Examiner* — Devang Thakor (57) ABSTRACT

Tablets and other objects are film coated by including in the tablet a film-forming polymer that is activated upon contact with an activating amount of liquid. The film-forming polymer, e.g., a cellulosic ether, is homogeneously mixed with the other ingredients of the tablet, shaped into any desirable form, loaded into a conventional coating apparatus, and sprayed or foamed with an activating amount of fluid, e.g., water, alcohol, etc., and dried. This coating process eliminates potential problems such as spray nozzle clogging, inappropriate coating fluid viscosity, and the inability to properly atomize the coating fluid. This coating process does not impart any appreciable weight or thickness gain to the tablet.

6 Claims, 11 Drawing Sheets

FIGURE 1

Uncoated Tablet

FIGURE 2

Coated Tablet with Coating Layer Intact

FIGURE 3

Coating Peeled Back (60 Minutes of Coating Time)

FIGURE 4

Coating Peeled Back (60 Minutes of Coating Time)

FIGURE 5

Coating Peeled Back (60 Minutes of Coating Time)

FIGURE 6

20 Minutes of Coating Time

FIGURE 7

60 Minutes of Coating Time

FIGURE 8

Comparison of Uncoated Tablet Weight and Tablet Weight
After 180 Minutes of Coating Time Using Process of the Invention

FIGURE 10

Comparison of Uncoated Tablet Weight and Tablet Weight
After 180 Minutes of Coating Time Using Conventional Coating Process

FIGURE 9

Comparison of Uncoated Tablet Thickness and Tablet Thickness
After 180 Minutes of Coating Time Using Process of the Invention

FIGURE 11

Comparison of Uncoated Tablet Thickness and Tablet Thickness
After 180 Minutes of Coating Time Using Conventional Coating Process

FIGURE 12

Drug Dissolution Testing Results from Tablets
Prepared from Example 2 (Formula 1) and Example 3 (Formula 2)

FIGURE 13

High Definition Images Printed on Tablet
Coating Using Process of the Invention

FIGURE 14

Tablet Containing 5wt% Ethylcellulose Activated with
50:50 by Volume Solvent Blend of Isopropyl Alcohol and Water

FIGURE 15

Tablet Containing 10wt% Ethylcellulose Activated with
50:50 by Volume Solvent Blend of Isopropyl Alcohol and Water

FIGURE 16

Tablet Containing 20wt% Ethylcellulose Activated with
50:50 by Volume Solvent Blend of Isopropyl Alcohol and Water

FIGURE 17

Tablet Containing 40wt% Ethylcellulose Activated with
50:50 by Volume Solvent Blend of Isopropyl Alcohol and Water

FIGURE 18

Tablet Containing 100wt% Ethylcellulose Activated with
50:50 by Volume Solvent Blend of Isopropyl Alcohol and Water

FIGURE 19

Tablet Containing 5wt% Ethylcellulose
Activated with Solvent of 100% Isopropyl Alcohol

FIGURE 20

Tablet Containing 10wt% Ethylcellulose
Activated with Solvent of 100% Isopropyl Alcohol

FIGURE 21

Tablet containing 20wt% ethylcellulose
Activated with Solvent of 100% Isopropyl Alcohol

FIGURE 22

Tablet Containing 40wt% Ethylcellulose
Activated with Solvent of 100% Isopropyl Alcohol

FIGURE 23

Tablet Containing 100wt% Ethylcellulose
Activated with Solvent of 100% Isopropyl Alcohol

US 8,778,399 B2

IN SITU, LIQUID-ACTIVATED FILM COATED TABLETS AND A PROCESS FOR MAKING THE SAME

CROSS REFERENCE TO RELATED APPLICATIONS

This application is a 35 USC §371 national phase filing of PCT/US2008/065478 filed Jun. 2, 2008, which claims the benefit of U.S. Ser. No. 60/948,110, filed Jul. 5, 2007.

FIELD OF THE INVENTION

This invention relates to film coatings. In one aspect, the invention relates to film coatings for tablets while in another aspect, the invention relates to a process for forming a film coating on a tablet. In still another aspect, the invention relates to tablets and other objects comprising a film coating.

BACKGROUND OF THE INVENTION

The conventional process for coating a tablet or similar item, e.g., a cereal food shape, confectionery item, etc., comprises spraying or foaming a coating, typically a film-forming polymer onto a tablet core while the core is tumbled or otherwise moved within a coating drum or similar piece of equipment. This process entails, among other things, forming a mixture of the coating polymer in a carrier solvent, e.g., water, alcohol, etc., applying the mixture to the tablet surface, and drying the coated tablet. This process is well known, and is described, for example, in U.S. Pat. Nos. 3,981,984, 4,828, 841 and many other similar teachings. If the coating process could eliminate the use of a polymeric coating liquid, the cost and time of manufacturing a coated tablet could be considerably reduced.

BRIEF SUMMARY OF THE INVENTION

In one embodiment, the invention is a product comprising a core and a film coating, the core and film coating each having a chemical composition that is essentially the same as the other. The core is typically a powder mixture but it can comprise virtually anything as long as it comprises a film-forming polymer. The film coating is typically of an essentially uniform thickness that fully covers the core although the thickness of the film coating can vary about the core, and film coating can cover less than the full surface area of the core. The product can be of any size and shape, it can be edible or inedible, and it can be further processed, e.g., printed, packaged, etc., or not.

In another embodiment the invention is a process of making a product that comprises a core and a film-coating, the process comprising the steps of (i) preparing a core from a material comprising a film-forming polymer, and (ii) activating the film-forming polymer in the core by contacting the core with an activating fluid. The film-forming polymer, e.g., a cellulosic ether, is homogeneously mixed with the other ingredients of the tablet, shaped into any desirable form, loaded into a conventional coating apparatus, and sprayed or foamed with an activating amount of fluid, e.g., liquid water or steam, liquid or gaseous alcohol, etc., and dried. This film coating process eliminates such potential problems as spray nozzle clogging, inappropriate coating liquid viscosity, and the inability to properly atomize the coating liquid. In turn, the elimination of these potential problems, and the very step of mixing the coating fluid, reduces the cost of the coating process. The process of this invention is appropriate for use in a wide variety of applications including, but not limited to, controlled-release matrix formulations, any solid dosage formulation, food cereal products, confectionery items, water-treatment and detergent-containing tablets, and the like.

The film coated products are unique in that the chemical composition of the film coating is the same or essentially the same as that of the product core, and the product does not gain any significant size or weight during the film coating process. The product coatings exhibit comparable, if not superior, physical properties, such as hardness, gloss, printability and the like, as a conventionally prepared coating.

BRIEF DESCRIPTION OF THE DRAWINGS

Each of FIGS. 3-5 is an SEM of a tablet after sixty minutes of film coating time with the film coating peeled back from the tablet core.

DETAILED DESCRIPTION OF THE PREFERRED EMBODIMENT

The numerical ranges in this disclosure include all values from and including the lower and the upper values, in increments of one unit, provided that there is a separation of at least two units between any lower value and any higher value. As an example, if a compositional, physical or other property, such as, for example, molecular weight, viscosity, melt index, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, coating and tablet thickness and weight, molecular weight, and the amount of various components in the compositions or formulations used in the practice of this invention.

"Polymer" means a polymeric compound prepared by polymerizing monomers, whether of the same or a different type. The generic term polymer thus embraces the term homopolymer, usually employed to refer to polymers prepared from only one type of monomer, and the term interpolymer as defined below.

"Copolymer", "interpolymer" and like terms means a polymer prepared by the polymerization of at least two different types of monomers. These generic terms include the traditional definition of copolymers, i.e., polymers prepared from two different types of monomers, and the more expansive definition of copolymers and interpolymers, i.e., polymers prepared from more than two different types of monomers, e.g., terpolymers, tetrapolymers, etc.

"Film coating" and like terms mean a skin or membranous coating, formed from the film-forming polymer when contacted with an activating fluid, e.g., liquid or gaseous water or organic compound such as an alcohol or another component of the activating fluid.

"Blend" and like terms mean a composition of two or more materials. Such a blend may or may not be miscible. Such a blend may or may not be phase separated. Such a blend may or may not contain one or more domain configurations, as determined from transmission electron spectroscopy, light scattering, x-ray scattering, and any other method known in the art.

"Activating fluid" and like terms mean a liquid or gas, that upon contact with a film-forming polymer, will convert the polymer into a film.

"Composition" and like terms means a mixture or blend of two or more components. In the context of a formulation from which a tablet and/or coating is fabricated, the composition includes all the components of the mix, e.g., active agent, binder, film-forming polymer, plasticizer and any other additives such as crosslinking agents and coagents, i.e. promoters or co-initiators or cure catalysts, antioxidants, fillers, non-tackifiers, colorants, pigments, lubricants, etc.

"Dosage form" and like terms means a material in a prescribed amount in the form of a tablet, pellet, capsule, lozenge and the like. The physical size of the dosage form can vary widely, but the amount of active ingredient is the amount necessary to perform the desired function of the form. For pharmaceutical and medicinal dosage forms, the active ingredient is typically a small component on a weight basis of the entire form. For industrial and commercial dosage forms, e.g., laundry tablets, water purification pellets, etc., the active ingredient can comprise all or essentially all of the form on a weight basis.

"Tablet", "pellet" and like terms means an article of manufacture typically formed by the compression of finely divided particles into a greater whole. The tablets of this invention can be of any size and shape although they are typically sized for human or animal consumption. The tablets of this invention can comprise a wide range of ingredients including pharmaceutically active agents and food, exemplary uses of such tables include medicinal and vitamin delivery systems, cereal products, confectionery items such as gum balls and candy pieces, and various industrial products such as soap for use in washing machines, water softener salt, water sanitation chemicals and the like.

The phrase "core and film coating having a chemical composition that are essentially the same as the other" means that the only substantial difference in the chemical composition of the core and the film coating is that the film-forming polymer of the film coating is hydrated or otherwise activated and the film-forming polymer in the core is not hydrated or otherwise activated. If all of the ingredients comprising the core are distributed throughout the core in an essentially homogeneous manner before activation of the film-forming polymer, then the relative amounts of the ingredients are the same in both the core and film coating after activation of the film-forming polymer.

The tablets of this invention can be formed by any process, and they are usually formed using any one of the conventional technologies, i.e., wet granulation, dry granulation and direct compression. Typical wet granulation includes the steps of milling the individual dry ingredients either alone or in combination with one another to a powder consistency, mixing the milled powders, preparing a binder solution, mixing the binder solution with the combined milled powders to form a wet mass, screening the mass, drying the screened and wet granules, drying the granules, and screening the dry granules with a lubricant and/or disintegrant. Tablets are made by compression of the granules. Dry granulation comprises similar steps except without the use of heat or solvent, and it is usually used when one or more tablet ingredients is sensitive to heat and/or solvent.

Direct compression is simply the compressing of a powder blend comprising the tablet ingredients without the pretreatment of the ingredients, e.g., screening, drying, etc. The powder blend itself is prepared simply by forming a preferably homogeneous blend of the individual ingredients using conventional mixing techniques and equipment.

In all these tablet formation techniques, the tablet compression step is essentially the same. The granulated or compressed tablet formulation is fed into a tablet die cavity, subjected to sufficient pressure to produce a tablet that will retain its shape and integrity through normal storage and handling until use, and removed from the die cavity. Once out of the die cavity, the tablet is cleaned of any fines, collected, packaged and stored.

One hallmark of this invention is that all of the tablets comprise a film-forming polymer. Any polymer that will form a film when contacted with an appropriate activating fluid can be used in the practice of this invention, and useful polymers include homo- or copolymers of ethylene imine, unsaturated acids such as acrylic acid or a salt thereof, unsaturated amides such as acrylamide, vinyl polymers such as vinyl alcohol, vinyl esters such as vinyl acetate, vinyl pyrrolidone, vinyl oxazolidone, vinyl methyloxazolidone, ethylene sulfonic acid, vinyl amine, vinyl pyridine, alkyl glycols, polyalkylene oxides such as polyethylene oxide and oxyethylene alkylether, polysaccharides and gelatins. Water-soluble polymers are preferred.

Examples of polysaccharides include gum arabic, xanthan gum, gum karaya, gum tragacanth, gum ghatti, carrageenan, dextran, alginates, agar, gellan gum, gallactomannans such as guar gum, pectins, starches, starch derivatives, guar derivatives and xanthan derivatives. Starch derivatives, guar derivatives and xanthan derivatives are described in more detail in European patent EP 0 504 870 B, page 3, lines 25-56 and page 4, lines 1-30. Useful starch derivatives are, for example, starch ethers such as hydroxypropyl starch or carboxymethyl starch. Useful guar derivatives are, for example, carboxymethyl guar, hydroxypropyl guar, carboxymethyl hydroxypropyl guar and cationized guar. Preferred hydroxypropyl guars and their production are described in U.S. Pat. No. 4,645,812, columns 4-6. Preferred polysaccharides are cellulose esters and cellulose ethers. Preferred cellulose ethers are carboxy-$C_1$-$C_3$-alkyl celluloses such as carboxymethyl celluloses; carboxy-$C_1$-$C_3$-alkyl hydroxy-$C_1$-$C_3$-alkyl celluloses such as carboxymethyl hydroxyethyl celluloses; $C_1$-$C_3$-alkyl celluloses such as methylcelluloses; $C_1$-$C_3$-alkyl hydroxy-$C_{1-3}$-alkyl celluloses such as hydroxyethyl methylcelluloses, hydroxypropyl methylcelluloses or ethyl hydroxyethyl celluloses; hydroxy-$C_{1\text{-}3}$-alkyl celluloses such as hydroxyethyl celluloses or hydroxypropyl celluloses; mixed hydroxy-$C_1$-$C_3$-alkyl celluloses such as hydroxyethyl hydroxypropyl celluloses, and alkoxy hydroxyethyl hydroxypropyl celluloses, the alkoxy group being straight-chain or branched and containing 2 to 8 carbon atoms. Most preferably, the fluid composition comprises water-soluble cellulose ether, such as a methylcellulose with a methyl molar substitution $DS_{methoxyl}$ of from 0.5 to 3.0, preferably from 1 to 2.5, or a hydroxypropyl methylcellulose with a DSmethoxyl of from 0.5 to 3.0, preferably from 1 to 2.5, and a $MS_{hydroxypropoxyl}$ of from 0.05 to 2.0, preferably from 0.1 to 1.5.

The polysaccharides, gelatins and the above-mentioned synthetic polymers generally have a weight average molecular weight of at least 10,000, preferably at least 12,000, more preferably at least 15,000. The preferred upper limit for the weight average molecular weight largely depends on the type of polymer. Generally the weight average molecular weight of the polymer is up to 1,000,000, preferably up to 500,000, more preferably up to 100,000.

Typically the film-forming polymers used in the practice of this invention comprise at least 1, preferably at least 5, more preferably at least 10 and most preferably at least 20 percent by weight of the tablet or other product composition. The maximum amount of the film-forming polymers used in the practice of this invention can vary to convenience and is typically a function of expense and practicality. Typically, the maximum of film-forming polymer used in the practice of this invention does not exceed 95, preferably it does not exceed 75 and more preferably it does not exceed 50, percent by weight of the tablet or other product composition.

The activating fluid used in the practice of this invention can be any liquid or gas that will activate the film-forming polymer upon contact with it, i.e., cause the film-forming polymer to form a film. Preferred compositions of the activating fluid mainly depend on the type of film-forming polymer, i.e. the manner of activating the film-forming polymer. Water-soluble film-forming polymers are generally activated with water. Organic-soluble film-forming polymers are generally activated when in contact with an appropriate organic solvent. The activating fluid can comprise a blend of water and organic solvent, e.g., a blend of water and an alcohol, and the relative amounts of each component in the blend can vary to convenience. The activating fluid can also comprise other ingredients, e.g., a surface tension lowering agent such as sodium lauryl sulfate to assist in the spread of the fluid over the surface of the tablet. Other additives include gloss enhancers, colorants and the like. In one particular embodiment of the invention, the activating fluid comprises a compound or agent that causes the film-forming polymer, or another compound or ingredient in the core, to swell. The activating fluid is applied using conventional coating equipment and techniques, and is applied in an amount sufficient to activate the film to form a film coating of desired thickness.

The activating fluids are typically and preferably compounds that liquid or gas under ambient conditions, e.g., atmospheric pressure and 23° C. For fluid-activated film-forming polymers, the activating fluid preferably is a monomeric compound or an oligomeric compound with a molecular weight of up to 500, preferably up to 300. Useful organic liquids are alcohols, preferably mono-functional alcohols, such as ethanol; alkenes, alkanes, halogenated alkenes, halogenated alkanes, ethers, esters and oils, such as paraffin oils, animal oils or vegetable oils. For water-activated film-forming polymers, preferably the coating liquid comprises at least 50, more preferably at least 75 and even more preferably at least 90, percent by weight water. Of course, the coating liquid is paired with the film-forming polymer to optimize the activation of the film-forming polymer.

One hallmark of this invention is that the film coating is formed by the activation of the film-forming polymer (in the case of a water-soluble film-forming polymer, the hydration) in the tablet core or matrix. In other words, the principal, if not the only, component of the film covering originates or is sourced in the core, not the activating fluid.

Another hallmark is that the film coatings of the tablets of this invention begin to form on the surface of the tablet core and then more toward the core center. As such, the tablet does not increase in any substantial manner in either weight or size, e.g., thickness. Any increase in weight is typically less than 5, more typically less than 2.5 and even more typically less than 1, percent of the original weight of the core. Likewise, any increase in thickness is typically less than 5, more typically less than 2.5 and even more typically less than 1, percent of the original thickness of the core. Typically the film coating has a thickness of less than 1000, more typically less than 500 and even more typically less than 200, micrometers.

Yet another hallmark is that the chemical composition of the tablet is essentially uniform throughout both the core and film coating with the understanding that the film-forming polymer in the matrix of the tablet is unactivated while the film-forming polymer in the coating is activated, i.e., in the physical form of a film.

Yet another feature of this invention is the absence of the need for the use of a plasticizer. One common, often essential, component of conventional coating formulations is the need for a plasticizer to facilitate a smooth and durable coating about the corners and edges of a tablet or other core shape. However, since the film coatings of this invention are formed from polymer already a part of the core, plasticizers are not needed to obtain a smooth and durable coating over these features of the core (although the activating fluid may contain one or more plasticizers if desired for any particular reason).

These unique features of the film coated tablets of this invention allow for the use of high molecular weight film-forming polymers as the source of the coating, e.g., polymers with a weight average (Mw) molecular weight in excess of 500,000, even in excess of 750,000 or 1,000,000. Due to the viscosity of high molecular weight film-forming polymers, these were considered too difficult to apply using conventional coating equipment and techniques and as such, the coatings typically comprised low molecular weight film-forming polymers. Films prepared from high molecular weight film-forming polymers often exhibit a better gloss than films prepared from low molecular weight film-forming polymers.

The film-forming polymer in the tablet matrix can serve multiple functions, e.g., in tablets that include an active ingredient, pharmacological or otherwise, the film-forming polymer can contribute to both the formation of the tablet coating and the control of the release of the active ingredient. In other embodiments, however, the tablet can include two or more film-forming polymers each with a different function, e.g., one to form the tablet coating and the other to control, or contribute to the control, of the immediate or controlled release of the active ingredient. In this context, the release of the active ingredient can be controlled, modified or delayed. Again, the advantage to this practice is that it avoids the preparation and spraying of viscous liquids.

Moreover, the film coatings of this invention impart a very desirable finish on the tablet surface, a finish that allows for the application of the edible printing commonly used in the pharmaceutical and food industries. This finish eliminates the issue of "logo bridging", i.e., the build-up of solid particulates from the coating liquid or foam that can occur on areas of the tablet surface on which the logo is printed or the surface is scored (i.e., indented). This bridging results in the loss of logo definition resulting in poor or inferior tablet appearance.

The film coated tablets of this invention and the process for making these tablets are further described by the following examples. Unless otherwise noted, all parts and percentages are by weight.

SPECIFIC EMBODIMENTS

Example 1

Round-shaped tablets (0.5 inch diameter) comprising METHOCEL™ A4MP cellulose ether (80 wt %), AVICEL™ PH-102 microcrystalline cellulose (19.5 wt %), and magnesium stearate (a lubricant, 0.5 wt %) are film coated in a laboratory scale coating pan (Vector Corporation of Marian, Iowa). METHOCEL™ A4MP cellulose ether is a premium grade methyl cellulose which is commercially available from The Dow Chemical Company and which has a methoxyl substitution of about 30 percent and an apparent viscosity of about 4,000 mPa·s, measured as a 2 weight percent aqueous solution. The coating liquid is water containing a blue food coloring and 0.001 percent by weight of sodium lauryl sulfate. The film coating conditions are an inlet temperature of 60-70C, outlet temperature of 30-40C, pan speed of 20-22 revolutions per minute (rpm), spray rate of 2-3 grams per minute (g/min), and a nozzle pressure of 17-25 pounds per square inch (psi). The film coated tablets are then subjected to scanning electron microscopy at different time intervals, and the results of these scans are reported in FIGS. 1-7.

Figure 1:
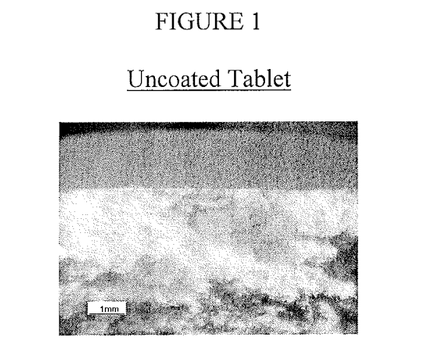
FIG. 1 is a scanning electron micrograph (SEM) of a cross-section of an uncoated tablet containing a film-forming polymer.
Figure 2:
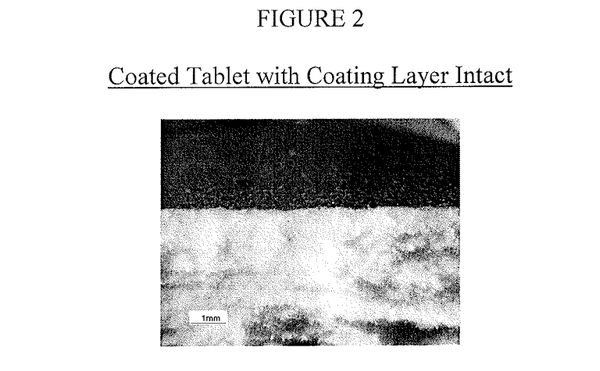
FIG. 2 is an SEM of the tablet of FIG. 1 film coated and with the film coating layer in tact using the inventive process.
Figure 3:
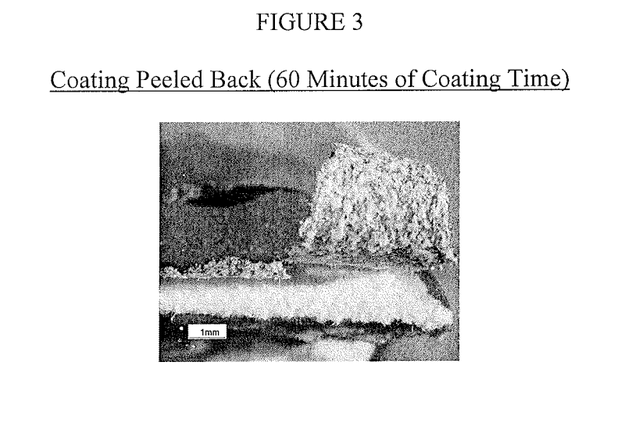
Figure 4:
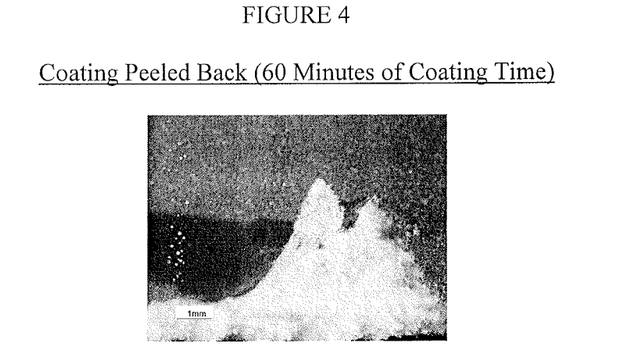
Figure 5:
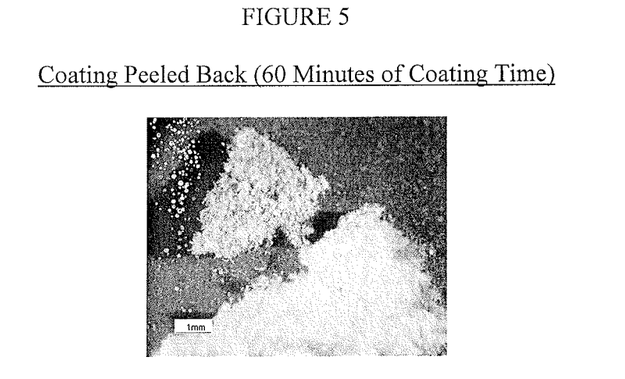
Figure 6:
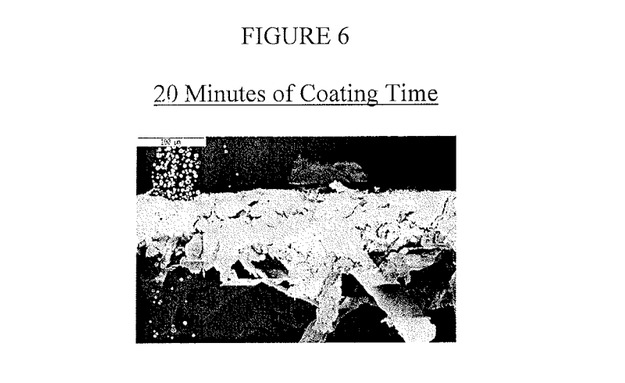
FIG. 6 is an SEM of a film coating cross-section after twenty minutes of film coating time.
Figure 7:
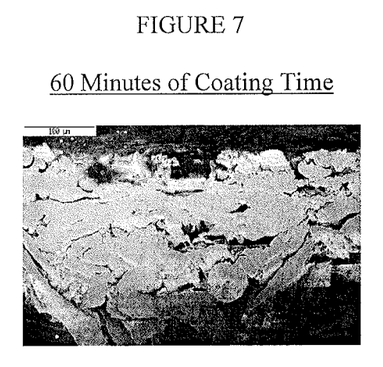
FIG. 7 is an SEM of a film coating cross-section after sixty minutes of film coating time.

FIG. 1 shows a cross-section of an uncoated tablet before application of the coating liquid. FIGS. 2-7 show tablets film coated using the process of this invention. FIG. 2 shows a cross-section of an intact, blue-colored tablet. FIGS. 3-5 show the blue-colored film coating peeled back from the tablet core or matrix to show the actual film coating that is formed from the hydration of the METHOCEL™ A4MP cellulose ether after 60 minutes of contact with water. FIGS. 6 and 7 show a cross-section of a film coating after 20 minutes and 60 minutes, respectively, contact with water. These figures show that the film coating begins at the surface of the uncoated tablet, and then grows inward toward the center of the tablet core. The ultimate percent thickness of the film coating of the product is a function of the end-use of the product, e.g., durability, gloss, receptiveness to print, time-release of an active ingredient, and the like.

Figure 8:
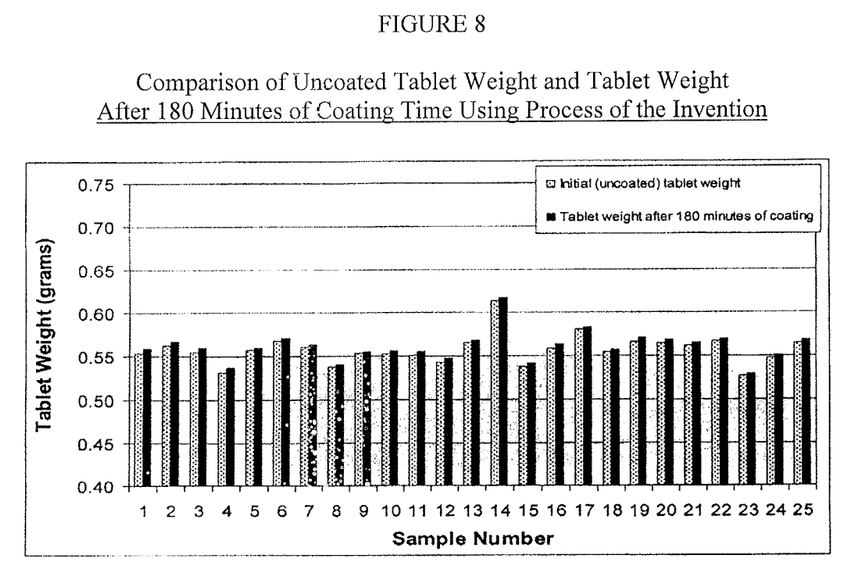
FIG. 8 is a bar graph reporting a comparison of the initial (uncoated) tablet weight and the tablet weight after 180 minutes of film coating application time using the process of this invention.
Figure 9:
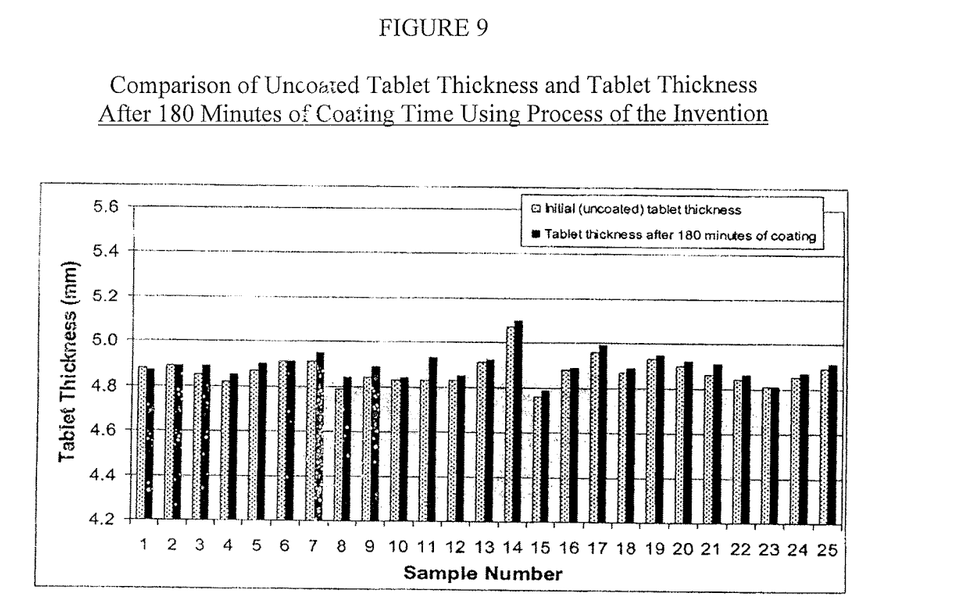
FIG. 9 is a bar graph reporting a comparison of the initial (uncoated) tablet thickness and the tablet thickness after 180 minutes of film coating application time using the process of this invention.
Figure 10:
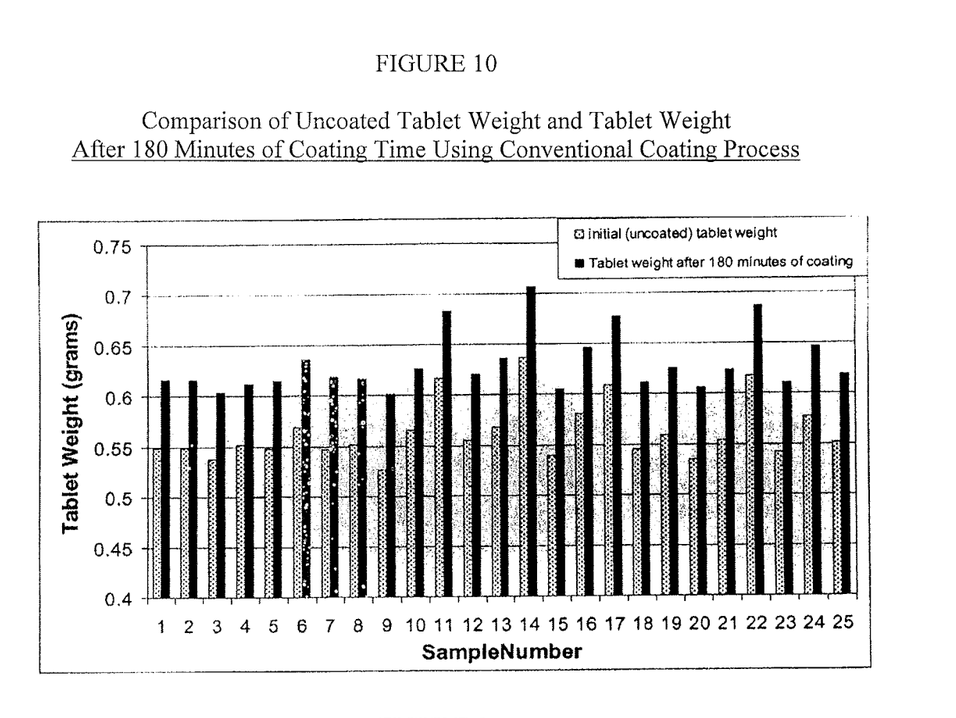
FIG. 10 is a bar graph reporting a comparison of the initial (uncoated) tablet weight and the tablet weight after 180 minutes of coating application time using a conventional coating process.
Figure 11:
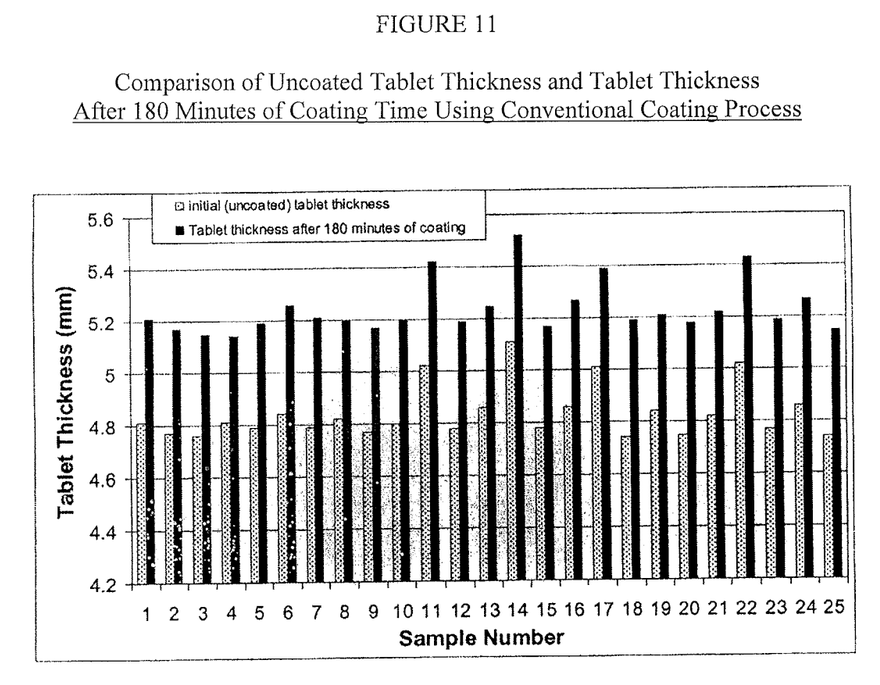
FIG. 11 is a bar graph reporting a comparison of the initial (uncoated) tablet thickness and the tablet thickness after 180 minutes of coating application time using a conventional coating process.

The thickness and weight of 25 film coated tablets are then measured, and the results are reported in FIGS. 8 and 9. These figures show little increase in both tablet weight and thickness during the formation of the film structure on the tablet surface even after 180 minutes of coating application time. This minimal increase in tablet weight and thickness reinforces the conclusion that the film is formed from the tablet matrix surface toward the center of the tablet matrix. This is just the opposite of conventional tablet coating where the film is formed from the tablet matrix surface outward, and this is supported by the measurable increases in tablet weight and thickness as reported in FIGS. 10 and 11. The conventional tablet coating liquid used in these comparative samples is a commercial tablet coating of Opadry™ YS-1-7006 available from Colorcon, Inc. of West Point, Pa. A 12 weight percent solution of this product is applied under the same coating conditions and with the same coating equipment as is used for the tablets prepared and reported in FIGS. 2-9.

Table 1 summarizes the information shown in FIGS. 8-11 as the average of 25 individual tablet measurements. As described in this table, a much greater weight in tablet weight and thickness is observed for tablets coated using conventional technology as compared with like tablets film coated with the process of this invention.

TABLE 1

Data Summary from FIGS. 8-11

| Method of Coating | Tablet Weight Gain (%) | Tablet Thickness Gain (%) |
|---|---|---|
| Invention | 0.64 | 0.54 |
| Conventional | 11.9 | 8.3 |

Examples 2-3

The film-forming polymer levels used in these examples are similar to those used in typical controlled-release pharmaceutical tablet formulations. The METHOCEL K4MP cellulose ether used in Examples 2 and 3 is a hydroxypropyl methylcellulose commercially available from The Dow Chemical Company which has a methoxyl substitution of 19-24 percent, a hydroxypropoxyl substitution of 7-12 percent and an apparent viscosity of about 4,000 mPa·s, measured as a 2 weight percent aqueous solution.

Example 2

| Controlled Release Tablet Formulation - Low Polymer Level | |
|---|---|
| Ingredient | %/Tablet |
| Acetaminophen (60-mesh) | 15.38 |
| METHOCEL K4MP | 20 |
| Lactose (Fast Flo) | 43.92 |
| Microcrystalline cellulose | 20 |
| FD&C Yellow No. 6 A1 Lake color | 0.2 |
| Magnesium stearate | 0.5 |

Example 3

| Controlled Release Tablet Formulation - High Polymer Level | |
| --- | --- |
| Ingredient | %/Tablet |
| Acetaminophen (60-mesh) | 15.38 |
| METHOCEL K4MP | 40 |
| Lactose (Fast Flo) | 23.92 |
| Microcrystalline cellulose | 20 |
| FD&C Yellow No. 6 A1 Lake color | 0.2 |
| Magnesium stearate | 0.5 |

Figure 12:
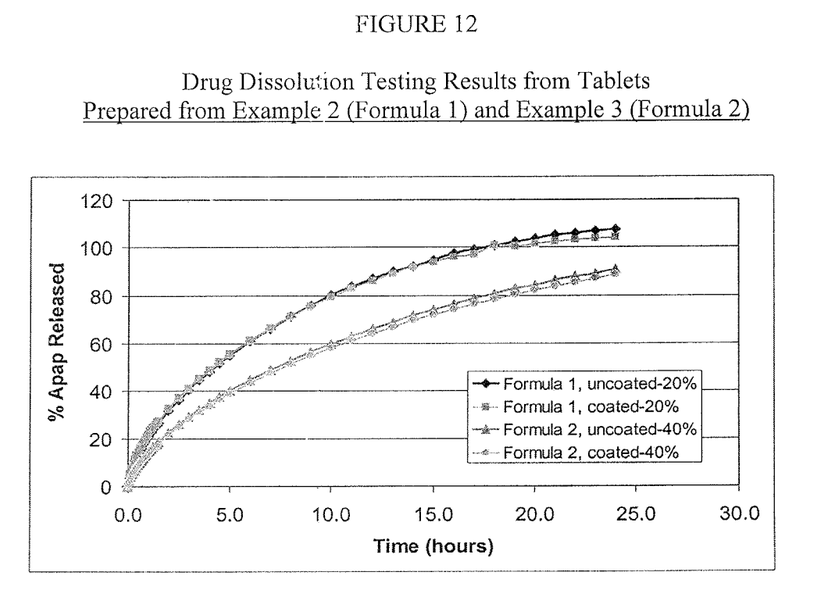
FIG. 12 is a line graph reporting a dissolution comparison of film coated and uncoated tablets having the same matrix formulation and film coated by the process of the invention.

The data of Examples 2 and 3 shows that the film coating process of the invention is useful in the preparation of typical matrix controlled-release dosage forms of medicinal products. Moreover, FIG. 12 shows that the film coating-finish applied to solid dosage forms does not alter the release profile of the tablet. FIG. 12 compares film coated and uncoated tablets having the same matrix formulation. These curves flatten over time which suggests a movement from first-order to zero-order release, a desirable result for controlled release formulations, i.e., over time, the active ingredient is released at a steady rate as opposed to either an accelerated or de-accelerated rate. The dissolution testing is conducted using a Varian Drug Dissolution Testing Model VK-7025 apparatus and 900 ml of deionized water at 37C+/−0.5C with agitation provided by paddles revolving at 50 rpm.

Example 4

Figure 13:
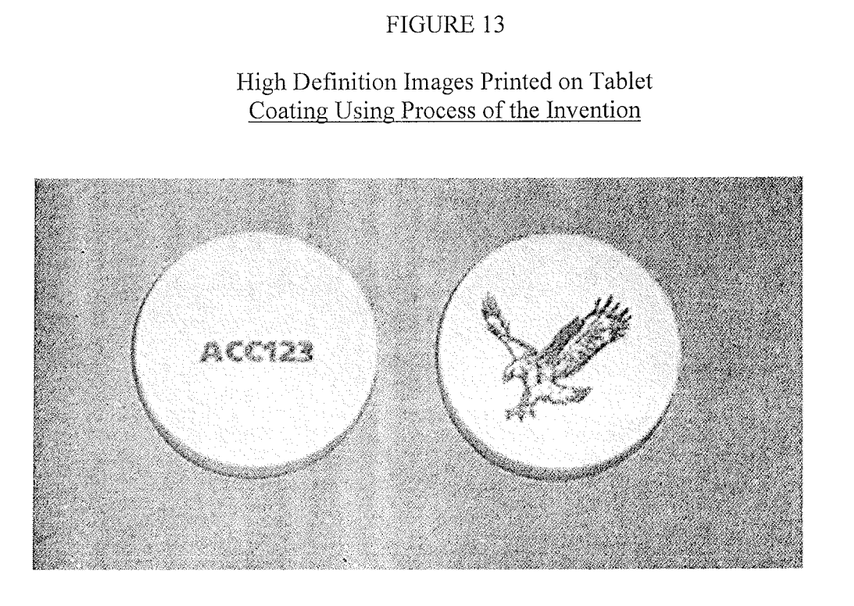
FIG. 13 shows two images of tablets film coated by the process of the invention bearing high definition designs printed using a high resolution tablet printer.
Figure 14:
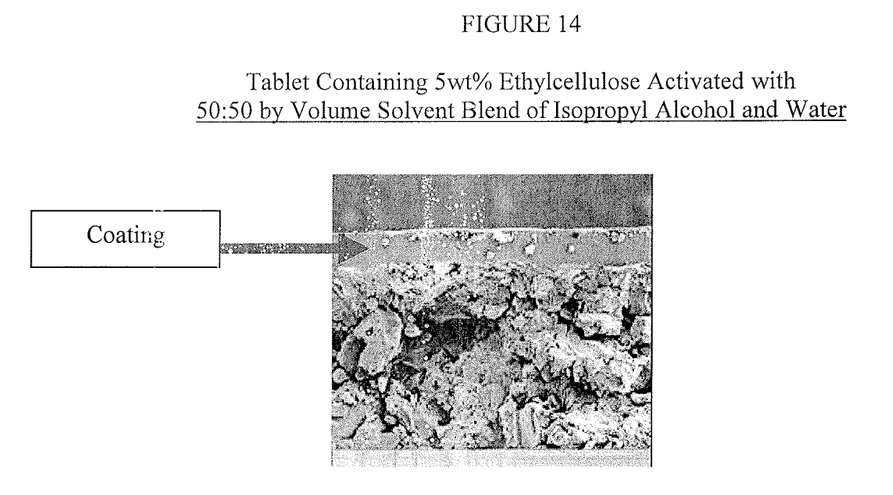
FIGS. 14-18 are SEM scans of tablet cross-sections showing the film coating layer over the tablet core of a tablets containing 5, 10, 20, 40 and 100 wt % ethylcellulose, respectively, after the film coated tablet precursor was contacted with a 50:50 by volume solvent blend of isopropyl alcohol and water.
Figure 15:
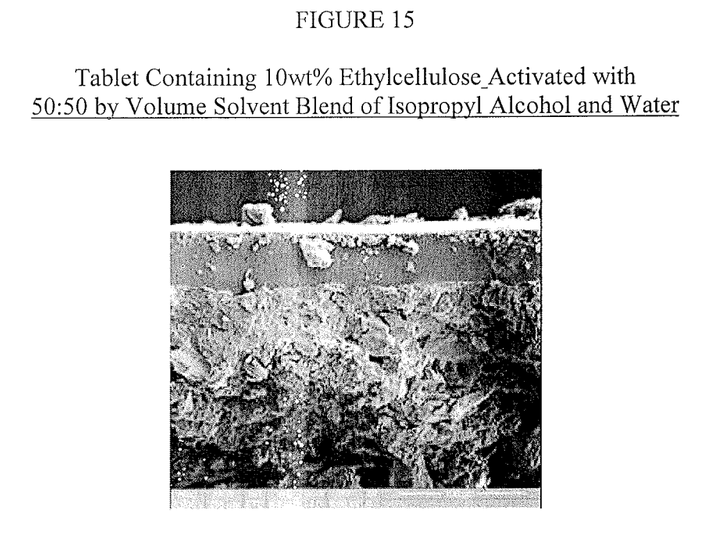
Figure 16:
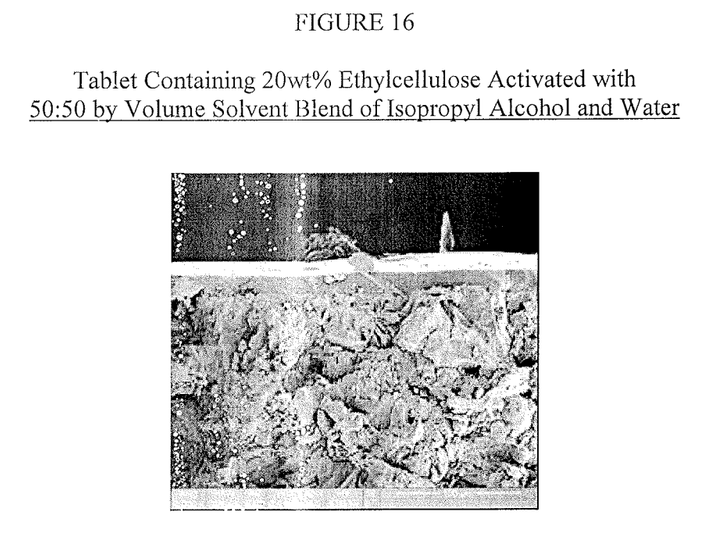
Figure 17:
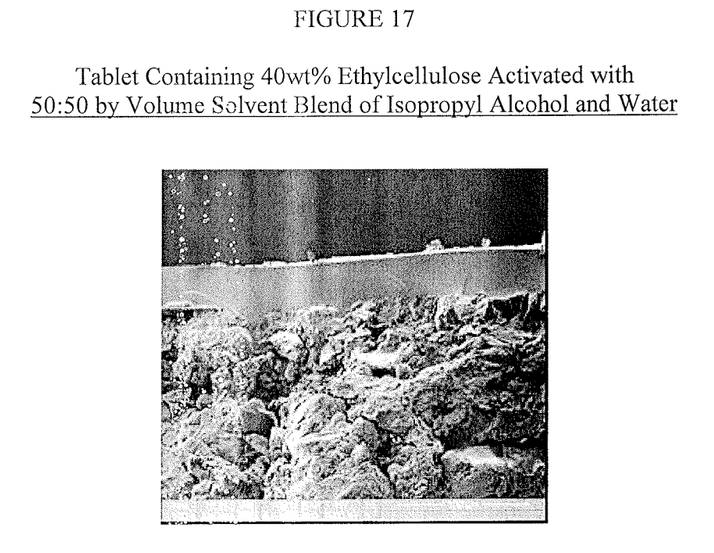
Figure 18:
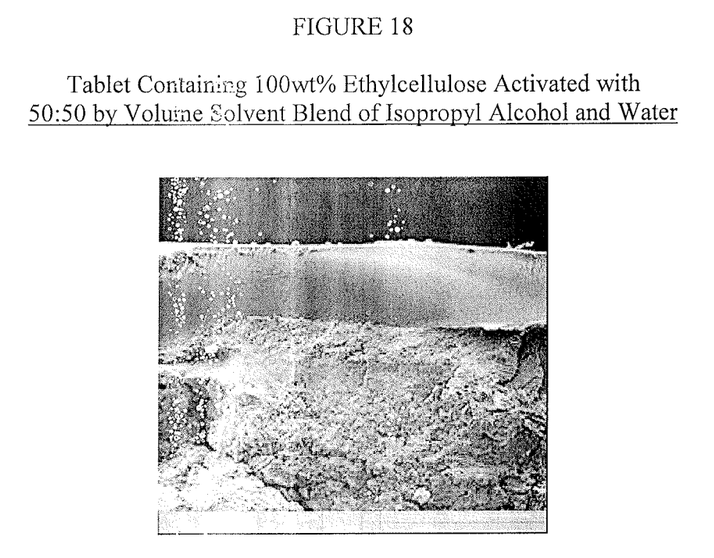
Figure 19:
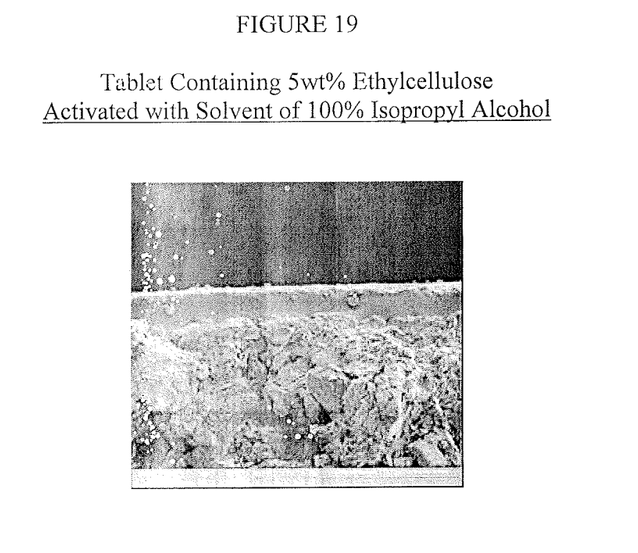
FIGS. 19-23 are SEM scans of tablet cross-sections showing the film coating layer over the tablet core of a tablets containing 5, 10, 20, 40 and 100 wt % ethylcellulose, respectively, after the film coated tablet precursor was contacted with a solvent of 100% isopropyl alcohol.
Figure 20:
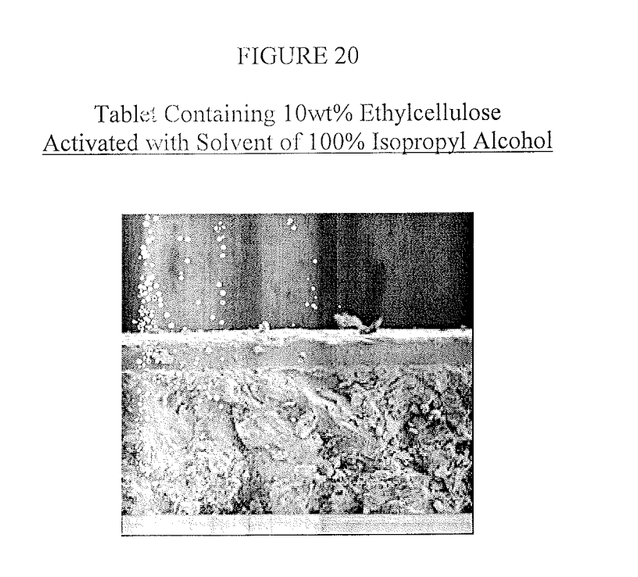
Figure 21:
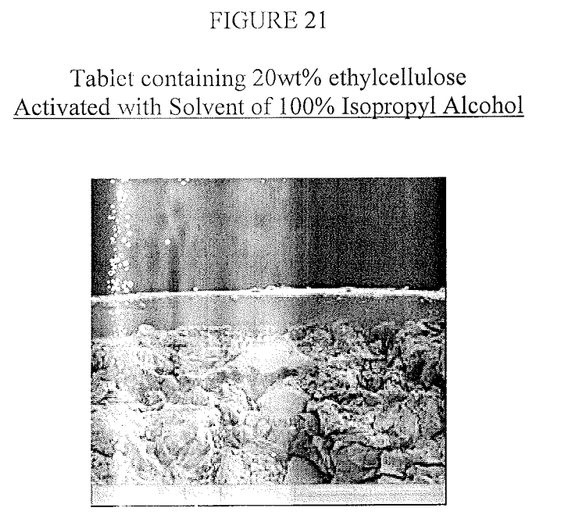
Figure 22:
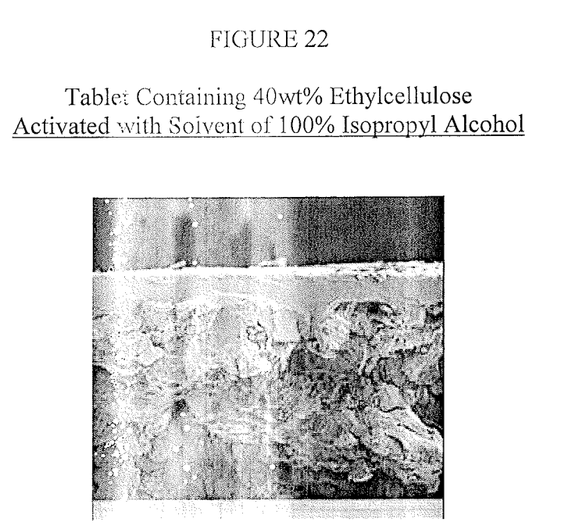
Figure 23:
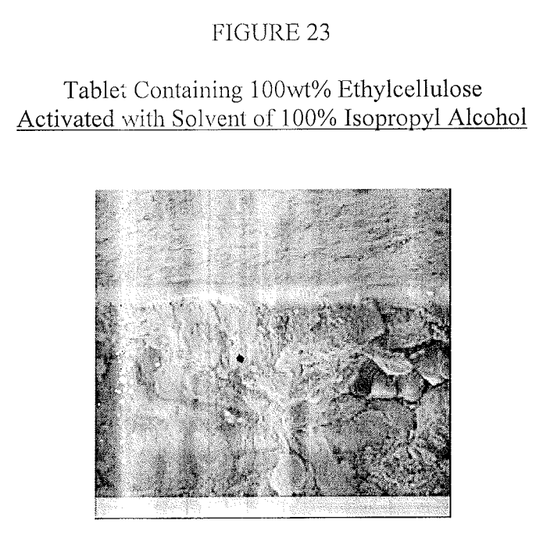

Placebo tablets prepared by the process of the invention are printed with a high definition, edible ink using a PI (model Platinum 160) High Resolution Laboratory Tablet Printer available from AC Compacting LLC of New Jersey. The two high definition designs are chosen to illustrate the integrity of the finish or film coating which if not present, allows the edible ink to soak into the tablet surface resulting in a smeared appearance. The printed tablets are reported in FIG. 13.

Examples 5 and 6

The following five formulations were prepared by blending all ingredients with one another until uniformly mixed, and then compressing the blended mixes into 650 mg tablets using a Carver Press equipped with 0.5 inch round standard concave tooling using a 4 thousand pound force with a two second dwell time. ETHOCEL Standard 10 Premium ethylcellulose is a film-forming polymer available from The Dow Chemical Company. The lactose and microcrystalline cellulose are present as fillers, and the magnesium stearate is present as a lubricant.

| Formulation 1 (5% Polymer) | | |
| --- | --- | --- |
| Ingredient | %/Tablet | mg/Tablet |
| ETHOCEL ethylcellulose | 5.0 | 32.5 |
| Lactose | 74.3 | 482.95 |
| Microcrystalline cellulose | 20.0 | 130.0 |
| Magnesium stearate | 0.5 | 3.25 |
| | 100% | 650 mg |

| Formulation 2 (10% Polymer) | | |
| --- | --- | --- |
| Ingredient | %/Tablet | mg/Tablet |
| ETHOCEL ethylcellulose | 10.0 | 65.0 |
| Lactose | 69.3 | 450.45 |
| Microcrystalline cellulose | 20.0 | 130.0 |
| Magnesium stearate | 0.5 | 3.25 |
| | 100% | 650 mg |

| Formulation 3 (20% Polymer) | | |
| --- | --- | --- |
| Ingredient | %/Tablet | mg/Tablet |
| ETHOCEL ethylcellulose | 20.0 | 130.0 |
| Lactose | 59.3 | 385.45 |
| Microcrystalline cellulose | 20.0 | 130.0 |
| Magnesium stearate | 0.5 | 3.25 |
| | 100% | 650 mg |

| Formulation 4 (40% Polymer) | | |
| --- | --- | --- |
| Ingredient | %/Tablet | mg/Tablet |
| ETHOCEL ethylcellulose | 40.0 | 130.0 |
| Lactose | 39.3 | 255.45 |
| Microcrystalline cellulose | 20.0 | 130.0 |
| Magnesium stearate | 0.5 | 3.25 |
| | 100% | 650 mg |

| Formulation 5 (100% Polymer) | | |
| --- | --- | --- |
| Ingredient | %/Tablet | mg/Tablet |
| ETHOCEL ethylcellulose | 100.0 | 650.0 |
| Lactose | 0.0 | 0.0 |
| Microcrystalline cellulose | 0.0 | 0.0 |
| Magnesium stearate | 0.0 | 0.0 |
| | 100% | 650 mg |

The tablets were film coated using conventional coating equipment from Vector Corporation. The tablets were sprayed with either a 50:50 by volume solvent blend of water and isopropyl alcohol or a solvent of 100% isopropyl alcohol for 180 minutes. FIGS. 14-18 show the formation of a film coating for all formulations sprayed with the 50:50 by volume solvent blend of water and isopropyl alcohol, and FIGS. 19-23 show the formation of a film coating for all formulations sprayed with the 100% isopropyl alcohol solvent.

Although the invention as been described in considerable detail by the preceding examples, this detail is for illustration and is not to be construed as a limitation on the spirit and scope of the invention as it is described in the following claims. All U.S. patents, U.S. patent application publications, allowed U.S. patent applications and all other references cited above are incorporated herein by reference.

What is claimed is:

1. A process of making a dosage form product that comprises a core and a film-coating, the process comprising the steps of
preparing a core from a pharmaceutically active ingredient and a material comprising a water-soluble, film-forming polymer with a weight average molecular weight of at least 12,000, wherein the film-forming polymer is a cellulose ester or a cellulose ether, compressing the core into a desired size and shape, and then coating the core by activating the film-forming polymer in the core by contacting the core with a sufficient amount of liquid activating fluid containing a surface tension lowering agent and at least 90 percent by weight water to hydrate the film-forming polymer into a film coating on the core, wherein no film-forming polymer is contained in the activating fluid, and wherein the core and film coating each have a chemical composition that is essentially the same as the other.

2. The process of claim 1 in which the film-forming polymer is a cellulose ether.

3. The process of claim 1 in which the film-forming polymer is homogeneously dispersed throughout the dosage form product.

4. The process of claim 1 in which the film forming polymer is methyl cellulose.

5. The process of claim 1 in which the film forming polymer is hydroxypropyl methylcellulose.

6. The process of claim 1 in which the surface tension lowering agent is sodium lauryl sulfate.

* * * * *